(12) United States Patent
Bunoz

(10) Patent No.: US 8,152,498 B2
(45) Date of Patent: Apr. 10, 2012

(54) PERISTALTIC PUMP WITH REMOVABLE TUBE

(75) Inventor: Etienne Vincent Bunoz, Eastbourne (GB)

(73) Assignee: Brightwell Dispensers Limited, East Sussex (GB)

( * ) Notice: Subject to any disclaimer, the term of this patent is extended or adjusted under 35 U.S.C. 154(b) by 406 days.

(21) Appl. No.: 12/453,360

(22) Filed: May 7, 2009

(65) Prior Publication Data

US 2009/0285706 A1 Nov. 19, 2009

(30) Foreign Application Priority Data

May 9, 2008 (GB) .................................. 0808481.6

(51) Int. Cl.
*F04B 27/08* (2006.01)
*F04B 1/12* (2006.01)
*F04B 43/12* (2006.01)

(52) U.S. Cl. ................... 417/477.3; 417/269; 417/477.1

(58) Field of Classification Search ............... 417/269, 417/477.1, 476, 475, 477.11, 477.3
See application file for complete search history.

(56) References Cited

U.S. PATENT DOCUMENTS

| 4,552,516 A | 11/1985 | Stanley |
| 2007/0031272 A1 | 2/2007 | Ramirez et al. |
| 2007/0148010 A1 | 6/2007 | Michels et al. |

FOREIGN PATENT DOCUMENTS

| DE | 2500463 | 7/1976 |
| FR | 2599434 | 12/1987 |
| GB | 1578022 | 10/1980 |

*Primary Examiner* — Joseph L Williams
(74) *Attorney, Agent, or Firm* — Levy & Grandinetti

(57) ABSTRACT

A peristaltic pump having a casing defining a tube race, a flexible tube disposed in the tube race, and a rotor with one or more rollers adapted to act against the flexible tube. The casing has a first section having the tube race and a first part of fitting means, and a second section having the rotor and a second part of the fitting means. The first and second parts of the fitting means are a releasable snap-fit together.

18 Claims, 3 Drawing Sheets

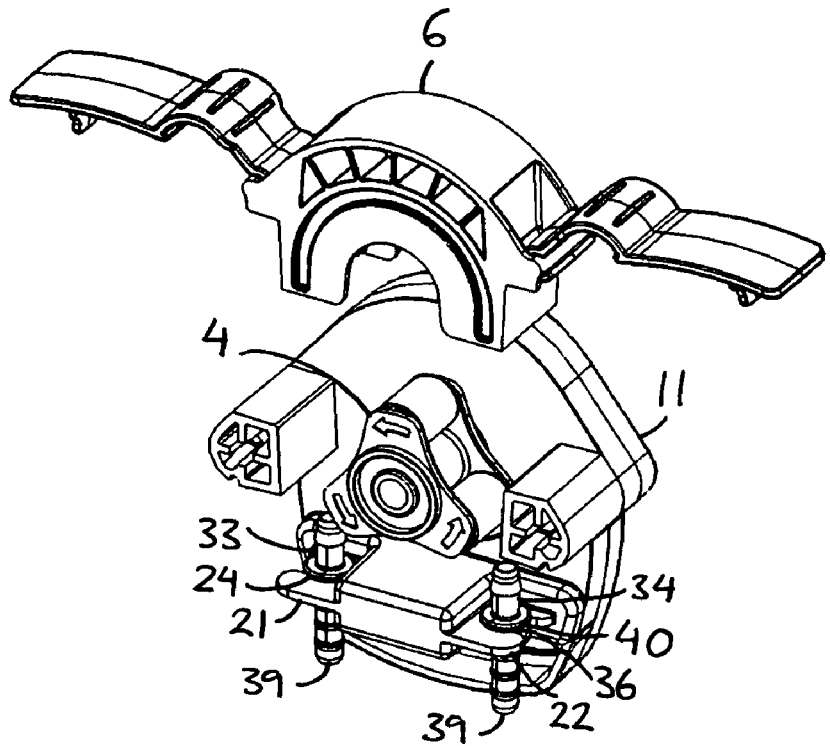
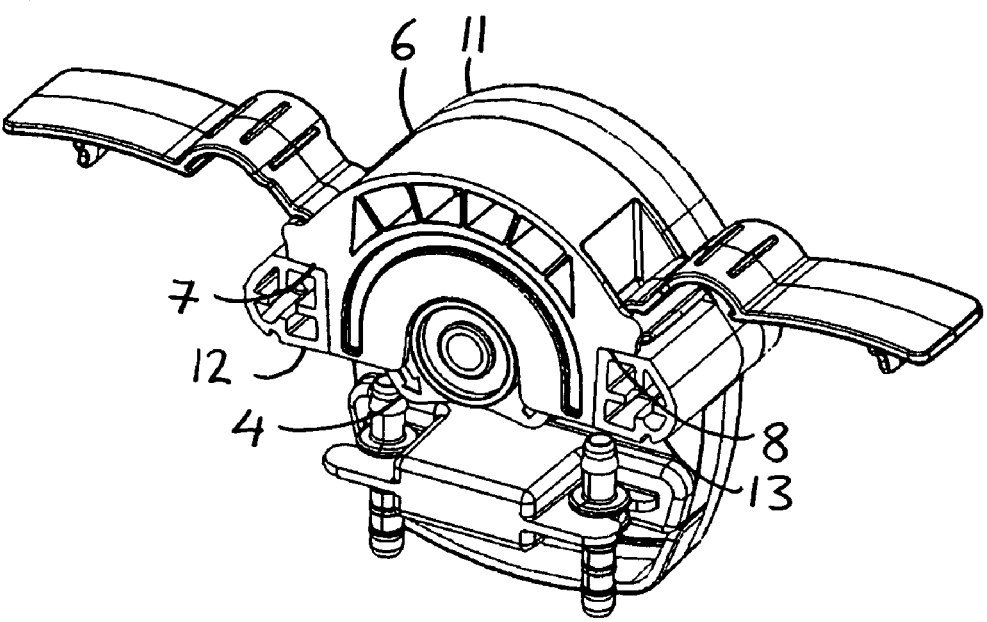

PERISTALTIC PUMP WITH REMOVABLE TUBE

The Applicant claims priority to Great Britain Application Number 0808481.6 filed on May 9, 2008.

This invention relates to a peristaltic pump with a removable tube, for use particularly, but not exclusively, as a 180 degree peristaltic pump used to pump chemicals and detergents for washing machines.

180 degree peristaltic pumps comprise a flexible tube housed in a semi-circular race, which is radially arranged about a rotor comprising a number of rollers which act on the tube to pump fluid therethrough.

The tubes are constructed from a hard wearing flexible material, however as they are constantly flexed they do wear out. In addition, where the fluids being pumped are caustic the working life of the tube is further reduced. When the tube expires in some known examples the whole pump unit is disposed of and replaced with another, as it is not cost effective to dismantle them and repair or replace the tube. However, this is obviously wasteful and expensive as the rest of the pump unit is usually in good order.

It is known to provide a mechanism by which the tube can be removed from a peristaltic pump, but such constructions comprise complex linkages, hinges and locking mechanisms which are costly to manufacture and to purchase. Such constructions are generally used in high end examples used in laboratories or for medical purposes.

The present invention is intended to overcome some of the above described problems.

Therefore, according to the present invention a peristaltic pump comprises a casing defining a tube race, a flexible tube disposed in said tube race, and a rotor with one or more rollers adapted to act against the flexible tube, in which the casing comprises a first section comprising said tube race and a first part of fitting means, and a second section comprising said rotor and a second part of said fitting means, in which the first and second parts of said fitting means are a releasable snap-fit together.

Thus, the present invention provides a peristaltic pump in which the casing can be dismantled to allow the tube to be replaced, by the expedient of a very simple snap-fitting.

In a preferred construction the first and second parts of the fitting means can be positioned such that when they are snap-fitted together the flexible tube is held inside the tube race by the rotor, and when the first and second parts of the fitting means are released from one another the first and second sections can be movable in relation to one another to such an extent that the flexible tube is removable from the casing.

It will be appreciated that the invention includes versions in which the first and second sections may be connected together in a hinged arrangement at a point away from the first and second parts of the fitting means, and the movement between the first and second sections can involve a rotation which moves the tube race away from the rotor.

However, in a preferred construction the first and second sections can be separate parts, and when the first and second parts of the fitting means are released from one another the first and second sections can be entirely removable from one another.

The invention includes pumps in which the first section is intended to be static, which is to say mounted to associated equipment, and the second section can be adapted to be removed therefrom. However, in a preferred construction the second section can be the static part. It can comprise a base comprising a surface, and the rotor can be mounted to the base and be adapted to rotate on an axis normal to said surface. The second part of the fitting means can comprise support means. In this construction the first section can comprise a cover defining said tube race, and the cover can be adapted to locate onto the base such that said tube race is radially arranged about the rotor. The first part of the fitting means can comprise location means adapted to co-operate with said support means.

In one version of the invention the support means can comprise a pair of arms parallel to said axis, each of which can be provided with a slot on the underside thereof. The location means can comprise a pair of shoulders adapted to rest on the arms, each of which can be provided with a resilient clip member adapted to ride over the corresponding arm and locate in the slot. It will be appreciated that the manner in which the first and second sections are fitted together must be robust because some known tubes are very thick and require considerable force to flex inside the tube race. The use of a pair of resilient snap-fit clips of this type is an adequately strong construction because the loading is transferred to the arms.

The ends of the flexible tube can simply extend out from the bottom of the pump, however in a preferred construction the base can be provided with two first parts of a releasable connection means, and second parts of said releasable connection means can be provided at either end of the flexible tube. As such, the ends of the tube can be held in position.

The first parts of said releasable connection means can each comprise a panel with a slot arranged in a plane which is parallel to said axis. In some versions of the invention the two slots can be arranged in different planes, which may suit particular plumbing arrangements, however preferably the two slots can be arranged in the same plane, so the ends of the tube extend out from the pump in the same direction.

The flexible tube can be provided with a connector at either end, and the second parts of the releasable connection means can comprise a connection portion of each connector, which can be adapted to be a resilient snap-fit in one of said slots. In addition, the connectors can each comprise positioning means adapted to co-operate with the corresponding panel to prevent axial movement of the connection portion in its slot. These positioning means can comprise an upper and a lower flange provided on each connector, which combine to define an annular trough adapted to receive the corresponding panel therein.

The slots can be forward facing, or they can face one another, however in a preferred construction the slots can comprise openings arranged normal to said surface, and said openings can face away from one another.

In one expedient version of the invention said slots can be arranged below said arms; each resilient clip member can be provided with a wing section comprising a tab on an underside thereof; and said slots can each comprise a secondary section adapted to releasably receive one of said tabs therein. As such, when the clip members are snap-fitted on the arms, the connectors can be locked into the slots by the tabs, which prevents inadvertent release of the ends of the flexible tube in use. In fact, as the loading generated in use acts to maintain the clip members in position on the arms, this loading also acts to keep the connectors in position.

The arms can comprise mounting bores adapted to receive bolts therethrough, such that the pump can be fittable to an actuator with which it is used. Rather than weakening the arms, this construction actually provides greater strength because the bolts can be strong metal components and they can be supported in position by the actuator.

The rotor can comprise a rotor bore adapted to receive a rotation crank provided as a part of the actuator. Preferably both the mounting bores and the rotor bore can extend through the whole length of the arms and the rotor respectively, such that the pump can be stackable on an actuator with which it is used along with other pumps of the same construction. Such stacking of peristaltic pumps is known.

In addition to this feature, the rotor can be provided with a basic spring clutch such that it is only rotatable by the crank in one direction, and is stationary when the rotor rotates in the opposite direction. This allows two stacked pumps to be arranged with oppositely mounted rotors so rotation of the crank in one direction pumps a first chemical, while rotation in the opposite direction pumps a second chemical. Again, this is a known arrangement.

Each of the connectors can comprises a head portion adapted to be fitted into one end of the flexible tube, and a hose tail adapted to be fitted into the end of an inlet or an outlet tube with which the pump is used. This construction allows for very ready fitment and release of inlet or outlet tubes.

In one construction the base can be provided with an end cover adapted to be releasably fitted to a second surface on an opposite side of the base to said surface. Such a cover prevents undue disturbance of the heads of the bolts and the end of the crank.

The invention can be performed in various ways, but one embodiment will now be described by way of example and with reference to the accompanying drawings, in which:

FIG. 3 is a perspective view of the peristaltic pump as shown in FIG. 1 in a first arrangement;

FIG. 4 is a perspective view of the peristaltic pump as shown in FIG. 1 in a second arrangement;

Figure 1:
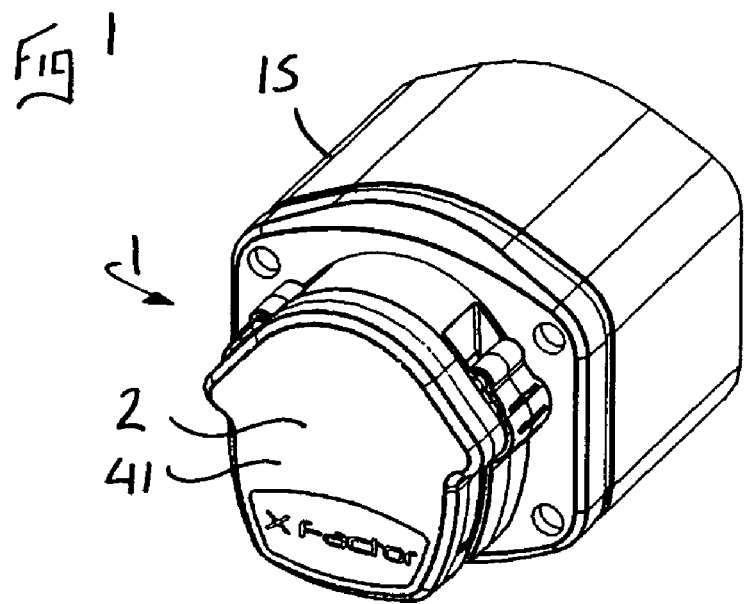
FIG. 1 is a perspective view of a peristaltic pump according to the invention mounted on an actuator.

As shown in the Figures, a peristaltic pump 1 comprises a casing 2 defining a tube race (not visible but indicated by the numeral 3), a flexible tube (not shown) disposed in said tube race 3, and a rotor 4 with three rollers 5 adapted to act against the flexible tube. As described further below, the casing 2 comprises a first section, in the form of cover 6, which comprises said tube race 3 and a first part of fitting means, in the form of shoulders 7 and 8 and resilient clip members 9 and 10, and a second section, in the form of base 11, which comprises said rotor 4 and a second part of said fitting means, in the form of arms 12 and 13. The clip members 9 and 10 and the arms 12 and 13 are a releasable snap-fit together.

Figure 2:
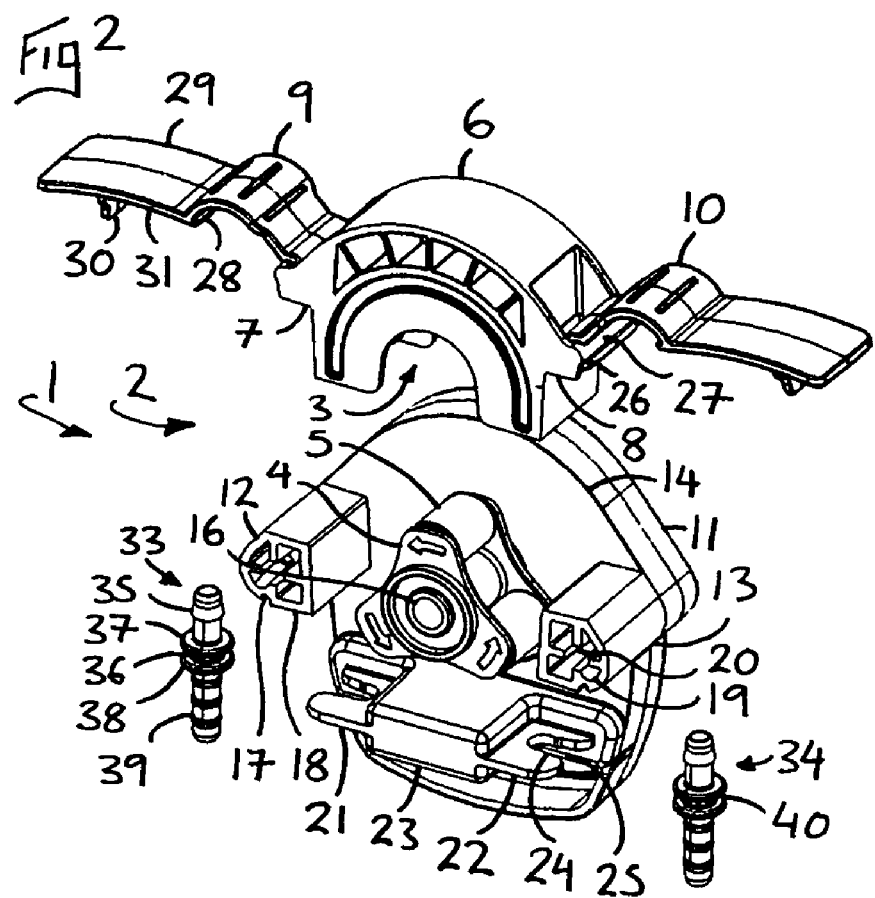
FIG. 2 is an exploded perspective view of the peristaltic pump as shown in FIG. 1.

As is clear from FIG. 2, the cover 6 and the base 11 are separate parts, which are entirely removable from one another.

The base 11 comprises a surface 14; the rotor 4 is mounted to the base 11, and, as is clear from the Figures, is adapted to rotate on an axis normal to said surface 14. (In practice the rotor 4 may not be mounted directly to the base 11, or perhaps only loosely by means of a simple annular locating boss disposed in an aperture provided in the base 11. Instead, the rotor 4 is "mounted to the base 11" due to the rotor 4 being mounted to a crank (not shown) provided as a part of the actuator 15 with which the pump 1 is used, and the base 11 enclosing the rotor 4 by being fitted to the actuator 15. As such, the rotor 4 forms a part of a static component of the pump 1 which is fitted to the actuator 15, while the cover 6 forms the removable part.) The rotor 4 is provided with a bore 16 which extends through its whole length, and which is adapted to receive the crank. The rotor also has an integral spring clutch (not visible) such that it is only rotatable by the crank in one direction.

The arms 12 and 13 extend normal to the surface 14 and are parallel to said axis. Each arm 12 and 13 is provided with a slot 17 on an underside 18 thereof, and a bore 19 which passes through its whole length. The bores 19 are provided with internal formations 20 adapted to co-operate with a mounting bolt or screw (not shown).

Below the arms 12 and 13 are the first parts of a releasable connection means, in the form of panels 21 and 22, which are part of a frame 23. Each panel 21 and 22 comprises a slot 24, and as is clear from the Figures the slots 24 are arranged in a plane which is parallel to said axis. The slots 24 comprise openings 25 which face away from one another.

Figure 5:
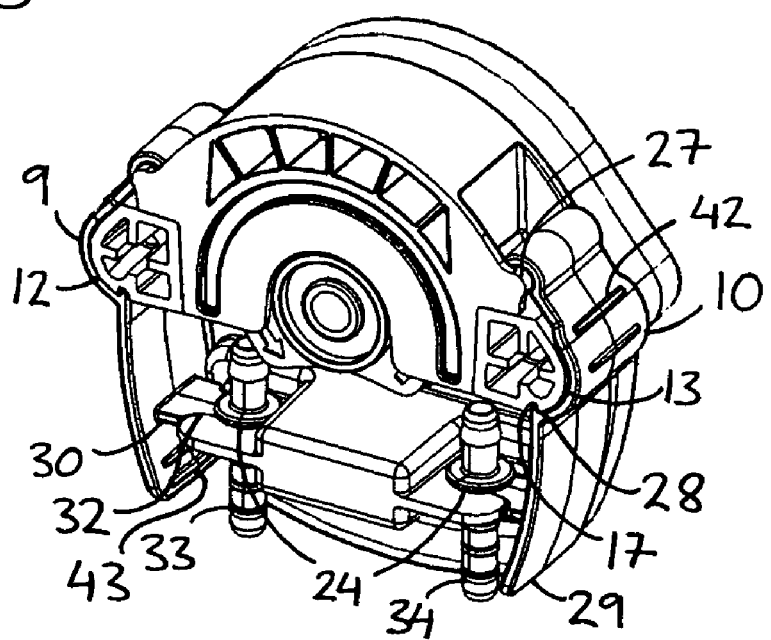
FIG. 5 is a perspective view of the peristaltic pump as shown in FIG. 1 in a third arrangement; and, FIG. 6 is a perspective view of two peristaltic pumps according to the invention stacked together and mounted on an actuator.

As is clear from FIG. 4 the shoulders 7 and 8 are adapted to fit onto the arms 12 and 13 such that the tube race 3 is held in a radial position about the rotor 4. Referring back to FIG. 2, each resilient clip member 9 and 10 comprises a sleeve 26 which is rotationally mounted on a bar 27 provided above each shoulder 7 and 8. When the cover 6 is mounted on the base 11 the bars 27 are parallel to said axis. Each clip member 9 and 10 also comprises an end 28 adapted to fit into the corresponding slot 17. The arms 12 and 13 are specifically shaped such that the ends 28 must ride over them, forcing the clip members 9 and 10 to flex, before the ends 28 snap into position in the slots 17, as shown in FIG. 5.

Each clip member 9 and 10 is provided with a wing section 29 comprising a tab 30 on an underside 31 thereof. The wing sections 29 operate as handles with which to manipulate the clip members 9 and 10 on and off the arms 12 and 13 in use. As is clear from FIG. 5, the tabs 30 are positioned such that they fit into secondary sections 32 of the slots 24 when the clip members 9 and 10 are snap-fitted to the arms 12 and 13.

Referring back to FIG. 2, the pump 1 further comprises connectors 33 and 34, each of which comprises head portion 35, connection portion 36, a pair of annular flanges 37 and 38, and hose tails 39. The head portions 35 are fitted into opposite ends of the flexible tube (not shown), and the hose tails 39 are adapted to receive the end of inlet or outlet tubes with which the pump 1 is used.

The connection portions 36 are annular sections which are adapted to be a releasable snap-fit in the slots 24. The two annular flanges 37 and 38 define an annular trough 40 between them which, as shown in FIG. 3, receives the panel 21 or 22 therein when the connection portions 36 are fitted into the slots 24, which prevents axial movement of the connectors 33 and 34 in use.

The flexible tube (not shown) can be provided with the connectors 33 and 34 already fitted, or the connectors 33 and 34 can be fitted just prior to use. As is clear from the Figures the head portions 35 are shaped to securely engage with the open end of a flexible tube.

The flexible tube (not shown) is dimensioned such that it extends from the area of one slot 24, around the rotor 4 and to the other slot 24.

Referring to FIG. 1, the base 11 is provided with an end cover 41 adapted to be releasably fitted to a second surface on an opposite side of the base 11 to said surface 14.

In use the pump 1 operates as follows. The base 11 is fitted to an actuator 15 with the surface 14 facing the actuator 15, by means of bolts (not shown) which pass through the bores 19 in the arms 12 and 13, and are secured in sockets (not visible) provided on the actuator 15. The rotor 4 is arranged between the base 11 and the actuator 15, and is mounted on a crank (not visible) which extends from the actuator 15. The end cover 41 can be fitted if desired.

A flexible tube (not shown) with the connectors 33 and 34 fitted into its ends is then passed down into the gap between the base 11 and the actuator 15, and positioned radially about the rotor 4. The connection portions 36 are then pushed into the corresponding slots 24 from the side, as shown in FIG. 3. The flexible tube is therefore positioned about the rotor 4, ready to be acted upon. Inlet and outlet tubes can then be fitted to the hose tails 39 as required.

The cover 6 is then slotted from above into the gap between the base 11 and the actuator 15, until the shoulders 7 and 8 are supported by the arms 12 and 13, as shown in FIG. 4. As such the tube race 3 (not visible in FIG. 4) is positioned radially about the flexible tube, supporting it so it can be acted upon by the rotor 4.

The clip members 9 and 10 are then rotated on the bars 27 such that the ends 28 thereof ride over the outside of the arms 12 and 13, forcing the clip members 9 and 10 to flex, until the ends 28 snap-fit into the slots 17, as shown in FIG. 5. This action can be achieved by pressing against the clip members 9 and 10, or by manipulating the wing sections 29. The clip members 9 and 10 are provided with grip bars 42 to facilitate this action. When this action occurs the tabs 30 enter the slots 24 and further secure the connectors 33 and 34 in the slots 24.

As such, the two sections 6 and 11 of the casing 2 are now fitted securely together, and the actuator 15 can be operated to rotate the rotor 4 and act on the flexible tube to pump fluid therethrough. During this action a loading is applied to the tube race 3 in a direction in which the cover 6 is releasable from the base 11. However, this loading is carried by the clip members 9 and 10, and as the ends 28 are orientated in the slots 17 in substantially the same direction as the loading, the loading acts to maintain the ends 28 in position in the slots 17, and thus keep the cover 6 in position. A lateral force is required to release the ends 28 from the slots 17, and this loading generates no such force.

During use the rotation of the rotor 4 will also generate a rotational force on the flexible tube. However, the tube is held in position by the secure fitment of the connectors 33 and 34 in the slots 24.

The flexible tube will last for several hundred hours of use, which in a typical installation might be spread over a 12 to 18 month period. When the flexible tube does wear out it can be readily replaced.

The clip members 9 and 10 are released from the arms 12 and 13 by manipulating the ends of the wing sections 29. The wing sections 29 are provided with grip bars 43 to facilitate this action. The wing sections 29 are pulled out laterally, forcing the ends 28 to leave the slots 17 and snap away therefrom.

The cover 6 is then lifted free from the base 11, as shown in FIG. 3. This exposes the flexible tube which needs to be replaced. The inlet and outlet tubes connected to the hose tails 39 are pulled free, before the connectors 33 and 34 are pulled laterally out from the slots 24. The flexible tube can then by lifted free from the pump 1 and disposed of.

A replacement flexible tube is then fitted into the pump 1 in the manner described above. The replacement tube may be provided with its own ready fitted connectors 33 and 34, or the connectors 33 and 34 can be removed from the old tube and reused.

Figure 6:
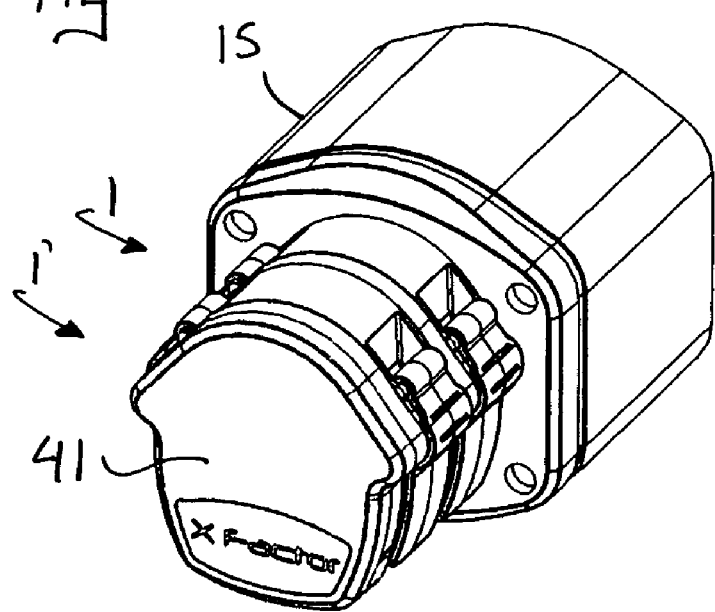

It is possible to use two peristaltic pumps together in a stack, as shown in FIG. 6. In this arrangement the first pump 1 is fitted to the actuator 15 and operated as described above, and the second pump 1' is fitted outside it. Longer bolts are used which pass through both sets of arms 12 and 13, and a longer crank is used, which passes through both rotors 4. The end cover 41 is fitted to the outside of the second pump 1'.

In this arrangement it is possible to operate the pumps 1 and 1' separately with the same crank due to the spring clutch incorporated into the rotors 4. The respective rotors 4 are mounted with their spring clutches arranged in opposite directions, so rotation of the crank in a first direction will rotate the first rotor 4, and rotation of the crank in a second direction will rotate the second rotor 4. Alternatively the rotors can be arranged with the spring clutches arranged in the same direction so they are both operated at the same time. It will be appreciated that any number of pumps 1 can be stacked together in this way, and arranged to operate in any configuration. The only limit to the size of the stack is the axial strength of the crank and the bolts.

The above described pump 1 is intended for use in pumping washing chemicals into industrial washing machines. However, it will be appreciated that this construction of peristaltic pump can be used wherever a peristaltic pump may be applicable, for example for general industrial purposes, for laboratory use and for medical use.

The above described pump 1 can be altered without departing from the scope of Claim 1. In particular, in one alternative arrangement (not shown) the cover is hinged to the base on one side, while the same kind of resilient snap-fit arrangement is provided on the other, such that when the snap-fit arrangement is released the cover is simply rotated away from the rotor to allow the flexible tube to be removed.

In another alternative arrangement (not shown) the first section comprising the tube race is static, which is to say it is mounted to associated actuator, and the second section comprising the rotor is removable therefrom.

Therefore, a peristaltic pump is provided which allows for the ready removal and replacement of the flexible tube component. In addition, the casing of the pump is robust and securely fitted together during use.

The invention claimed is:

1. A peristaltic pump comprising a casing defining a tube race, a flexible tube disposed in said tube race, and a rotor with one or more rollers adapted to act against the flexible tube, in which the casing comprises a first section comprising said tube race and a second section comprising said rotor, in which the second section comprises a pair arms, each of which is provided with a slot on the underside thereof, in which the first section comprises a pair of shoulders adapted to rest on the arms, each of which is provided with a resilient clip member adapted to ride over the corresponding arm and locate in the slot in a releasable snap-fit arrangement.

2. A peristaltic pump as claimed in claim 1 in which the arms and the shoulders are positioned such that when they are snap-fitted together the flexible tube is held inside the tube race by the rotor, and in which when the arms and the shoulders are released from one another the first and second sections are movable in relation to one another to such an extent that the flexible tube is removable from the casing.

3. A peristaltic pump as claimed in claim 2 in which when the arms and the shoulders are released from one another the first and second sections are entirely removable from one another.

4. A peristaltic pump as claimed in claim 3 in which the second section comprises a base comprising a surface, in which the rotor is mounted to the base and is adapted to rotate on an axis normal to said surface, in which the first section comprises a cover defining said tube race, in which the cover is adapted to locate onto the base such that said tube race is radially arranged about the rotor.

5. A peristaltic pump as claimed in claim 4 in which arms are parallel to said axis.

6. A peristaltic pump as claimed in claim 5 in which the base is provided with two first parts of a releasable connection means, in which second parts of said releasable connection means are provided at either end of the flexible tube, and are releasably fitted to a first part of said releasable connection means.

7. A peristaltic pump as claimed in claim 6 in which the first parts of said releasable connection means each comprise a panel with a slot arranged in a plane which is parallel to said axis.

8. A peristaltic pump as claimed in claim 7 in which the slots are arranged in the same plane.

9. A peristaltic pump as claimed in claim 8 in which the flexible tube is provided with a connector at either end, in which the second parts of the releasable connection means comprise a connection portion of each connector, which is adapted to be a resilient snap-fit in one of said slots.

10. A peristaltic pump as claimed in claim 9 in which the connectors each comprise positioning means adapted to co-operate with the corresponding panel to prevent axial movement of the connection portion in its slot.

11. A peristaltic pump as claimed in claim 10 in which each positioning means comprises an upper and a lower flange provided on each connector, which combine to define an annular trough adapted to receive the corresponding panel therein.

12. A peristaltic pump as claimed in claim 11 in which said slots comprise openings arranged normal to said surface, and in which said openings face away from one another.

13. A peristaltic pump as claimed in claim 12 in which said slots are arranged below said arms, in which each resilient clip member is provided with a wing section, in which each wing section comprises a tab on an underside thereof, and in which said slots each comprise a secondary section adapted to releasably receive one of said tabs therein.

14. A peristaltic pump as claimed in claim 13 in which said arms comprise mounting bores adapted to receive bolts therethrough, such that the pump is fittable to an actuator with which it is used.

15. A peristaltic pump as claimed in claim 14 in which the rotor comprises a rotor bore adapted to receive a rotation crank provided as a part of an actuator with which the pump is used.

16. A peristaltic pump as claimed in claim 15 in which the mounting bores and the rotor bore extend through the whole length of the arms and the rotor respectively, such that the pump is stackable on an actuator with which it is used along with other pumps of the same construction.

17. A peristaltic pump as claimed in claim 9 in which each connector comprises a head portion adapted to be fitted into one end of the flexible tube, and a hose tail adapted to be fitted into the end of an inlet or an outlet tube with which the pump is used.

18. A peristaltic pump as claimed in claim 4 in which the base is provided with an end cover adapted to be releasably fitted to a second surface on an opposite side of the base to said surface.

* * * * *